US 7,495,055 B2

(12) United States Patent
Soerens et al.

(10) Patent No.: US 7,495,055 B2
(45) Date of Patent: Feb. 24, 2009

(54) MULTI-PURPOSE ADHESIVE COMPOSITION

(75) Inventors: Dave Allen Soerens, Neenah, WI (US); Stephen Michael Campbell, Winneconne, WI (US); Jisheng Shen, Appleton, WI (US); David William Koenig, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 603 days.

(21) Appl. No.: 11/025,317

(22) Filed: Dec. 29, 2004

(65) Prior Publication Data

US 2006/0142445 A1  Jun. 29, 2006

(51) Int. Cl.
| | |
|---|---|
| C08L 83/00 | (2006.01) |
| C08L 83/06 | (2006.01) |
| C08K 5/00 | (2006.01) |
| C08K 5/16 | (2006.01) |
| C08K 5/09 | (2006.01) |
| C08K 5/10 | (2006.01) |
| C08K 5/17 | (2006.01) |

(52) U.S. Cl. .................. 524/588; 524/858; 524/81; 524/186; 524/306; 524/308; 524/320
(58) Field of Classification Search .................. 524/543, 524/588, 858, 81, 186, 306, 308, 320
See application file for complete search history.

(56) References Cited

U.S. PATENT DOCUMENTS

| | | | | |
|---|---|---|---|---|
| 4,251,400 | A * | 2/1981 | Columbus | ............... 524/24 |
| 5,018,337 | A * | 5/1991 | Carter et al. | ............... 53/458 |
| 6,737,491 | B2 | 5/2004 | Soerens et al. | |
| 6,849,685 | B2 | 2/2005 | Soerens et al. | |
| 2002/0034492 | A1 * | 3/2002 | Munro et al. | ............ 424/78.36 |
| 2002/0086942 | A1 * | 7/2002 | Fujita et al. | ................ 525/100 |
| 2003/0212416 | A1 | 11/2003 | Cinelli et al. | |
| 2003/0215630 | A1 * | 11/2003 | Melancon et al. | ..... 428/355 AC |
| 2004/0019168 | A1 | 1/2004 | Soerens et al. | |
| 2004/0043688 | A1 | 3/2004 | Soerens et al. | |
| 2004/0057986 | A1 | 3/2004 | Merrigan et al. | |
| 2004/0068093 | A1 | 4/2004 | Merrigan et al. | |
| 2004/0106721 | A1 * | 6/2004 | Soerens | ................... 524/445 |
| 2004/0115251 | A1 | 6/2004 | Goldman et al. | |

FOREIGN PATENT DOCUMENTS

| | | |
|---|---|---|
| EP | 1 163 309 B1 | 6/2004 |
| WO | WO 2004/011046 A1 | 2/2004 |
| WO | WO 2004/011048 A1 | 2/2004 |

OTHER PUBLICATIONS

Neumann, A.W., and R.J. Good, "Techniques of Measuring Contact Angles," Chapter 2, *Surface and Colloid Science—Experimental Methods*, vol. 11, edited by R.J. Good and R.R. Stromberg, Plenum Press, 1979, pp. 31-91.

* cited by examiner

*Primary Examiner*—Vasu Jagannathan
*Assistant Examiner*—Karuna P Reddy
(74) *Attorney, Agent, or Firm*—Bryan R. Rosiejka; Denise L. Stoker

(57) ABSTRACT

An adhesive composition comprises at least a binder polymer and a water-soluble plasticizer. The binder polymer may be present in a range of about 10% to about 60% by weight of the adhesive composition, and the plasticizer may be present in the range of about 5% to about 85% by weight of the adhesive composition, such as in the range of about 40% to about 80% by weight. In some aspects, the adhesive also comprises less than 10% by weight highly-volatile component, such as about 0% to about 5% by weight. The adhesive composition can be utilized in a variety of articles, including personal care articles, health/medical articles, and household/industrial articles.

27 Claims, No Drawings

MULTI-PURPOSE ADHESIVE COMPOSITION

BACKGROUND

Recent advances have been made in the field of hydrogel adhesives, particularly those adhesives that can be utilized on human skin. One intent of such adhesives is to provide consistent adhesion properties after subsequent detachments and re-attachments, while minimizing or eliminating the amount of adhesive residue left on the surface after each detachment. Such adhesives can involve the use of monomers and plasticizers, such as glycerol. Often, these adhesives are crosslinked using a procedure known as photopolymerization. Unfortunately, the use of such monomers and photopolymerization can often result in levels of residual monomer that are unknown until after the adhesive is prepared. Additionally, the photopolymerization procedure can produce toxic by-products, such as acrolein, when used in combination with glycerol. Therefore, there is a need for an adhesive composition which is based on a polymer with specified low levels and/or known levels of residual monomer, and which does not result in the production of toxic by-products.

Furthermore, the production of hydrogel adhesives such as those described above can be very cost-intensive. For example, such processes typically involve ultraviolet (UV) polymerization which requires, among other things, nitrogen purging and expensive UV lamps and photoinitiators. UV polymerized hydrogel adhesives are generally formed in unit sizes because the low viscosity monomers must be confined in a cell until the polymerization is complete. Therefore, there is a further desire for an adhesive composition made using a procedure that is less complex, that has lower capital requirements for a drying operation, and that is more amenable to large scale coating and drying with subsequent die cutting to shape.

A further issue with hydrogel adhesives such as those described above concerns the amount of water contained in the adhesives. For example, such hydrogel adhesives typically contain at least 10% water and as much as 85% water by weight. This high water content may be an issue because evaporation of the water, whether in storage or in use, can result in significant changes in the adhesion properties of the hydrogel adhesive. For instance, drying during storage can result in stiff adhesives with poor tack and compliance. Additionally, drying during use can result in significant adhesive build and painful removal. Therefore, there is a further need for an adhesive composition that contains very little water, thus minimizing water loss induced changes in adhesion property during storage or during use. Furthermore, it may be desirable to further incorporate certain additives into the adhesive composition which can be utilized to provide benefits to attachment surfaces, particularly additives such as medications and skin enhancers.

SUMMARY

The invention concerns adhesives, such as hydrogel adhesives. More particularly, the invention is directed to an adhesive composition which comprises at least a binder polymer and a water-soluble plasticizer. In desirable aspects, the binder polymer may be present in an amount of about 10% to about 60% by weight of the adhesive composition and the plasticizer may be present in an amount of about 5% to about 85% by weight of the adhesive composition, such as about 40% to about 80% by weight. In some aspects, the adhesive composition may also comprise less than 10% by weight highly-volatile component such as water, more suitably about 0% to about 5% by weight. The adhesive composition can be utilized in a variety of articles, including personal care articles, health/medical articles, and household/industrial articles.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body. The term "disposable" is used herein to describe absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "health/medical article" includes a variety of professional and consumer health-care products including, but not limited to, medicated patches, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial articles" include construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, cover-alls, trash bags, stain removers, topical compositions, laundry soil/ink absorbers, packagings, and the like.

The term "hydrophilic" refers to a material having a contact angle of water in air of less than 90 degrees. The term "hydrophobic" refers to a material having a contact angle of water in air of at least 90 degrees. For the purposes of this application, contact angle measurements are determined as set forth in Robert J. Good and Robert J. Stromberg, Ed., in "Surface and Colloid Science—Experimental Methods," Vol. II, (Plenum Press, 1979), herein incorporated by reference in a manner consistent with the present disclosure.

The phrase "personal care article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, pantyliners, panty shields, interlabials, tampons, and tampon applicators; adult-care products including wipes, pads such as breast pads, containers, incontinence products, and urinary shields; clothing components; bibs; athletic and recreation products; and the like.

These terms may be defined with additional language in the remaining portions of the specification.

DETAILED DESCRIPTION

The invention concerns adhesives, such as hydrogel adhesives. More particularly, the invention is directed to an adhesive composition which comprises at least a binder polymer and a water-soluble plasticizer. In desirable aspects, the binder polymer may be present in an amount of about 10% to about 60% by weight of the adhesive composition and the plasticizer may be present in an amount of about 5% to about 85% by weight of the adhesive composition, such as about 40% to about 80% by weight. In some aspects, the adhesive composition also comprises less than 10% by weight highly-volatile component, such as about 0% to about 5% by weight. Crosslinking of the constituents suitably takes place in the presence of the plasticizer, which creates a three dimensional matrix.

The binder polymer suitably includes about 15 to about 99.8% by weight of monoethylenically unsaturated polymer units, such as about 25 to about 90% by weight, or about 30 to about 80% by weight, or about 50 to about 70% by weight. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides (such as maleic anhydride);

c) Carboxylic acid salt group-containing monomers including water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

d) Sulfonic acid group-containing monomers, including aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth)acryloxy propyl sulfonic acid, 2-acrylamido-2-methyl-1-propane sulfonic acid];

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], 3-acrylamidopropyl trimethyl ammonium chloride, vinyl lactams (such as N-vinylpyrrolidone).

The binder polymer also includes about 0.1 to about 20% by weight of polyacrylate ester units, such as acrylate and/or methacrylate ester units, that include an alkoxysilane functionality. The acrylate and/or methacrylate ester units are copolymerized with the monoethylenically unsaturated monomer units. In particular, the binder polymer may include about 0.5 to about 15% by weight of the acrylate and/or methacrylate ester units, such as about 1.0 to about 10% by weight, or about 1.5 to about 5.5% by weight.

The alkoxysilane functionality is a functional group or moiety that reacts with water to form a silanol group. One suitable alkoxysilane group is a trialkoxy silane group having the following structure:

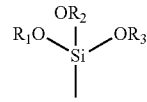

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates. A particularly ethylenically unsaturated monomer containing a trialkoxy silane functional group is methacryloxypropyl trimethoxy silane, commercially available from Dow Corning, a business having offices located in Midland, Mich. U.S.A. under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects and are effective monomers for copolymerization in accordance with the present invention.

The binder polymer also includes about 0.1-75% by weight polyolefin glycol and/or polyolefin oxide units, such as about 5-75% by weight, or about 10-60% by weight, or about 20-50% by weight, or about 30-40% by weight. The polyolefin glycol or oxide may be a glycol or oxide of an olefin polymer having about 2-4 carbon atoms. Polyethylene glycol, polyethylene oxide, polypropylene glycol and polypropylene oxide are examples of suitable polymer units. The polyolefin glycol and/or polyolefin oxide may include on average about 4 to 15,000 glycol and/or oxide units per molecule. The weight average molecular weight of polyolefin glycol units may range from about 200 to 8,000. When polyolefin oxide units are employed, they may have a weight average molecular weight of about 100,000 to about 600,000.

Polyolefin glycols and polyolefin oxides are commercially available, and are common. To prepare the binder polymer of the invention, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting binder polymer includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation, thermal energy, ultraviolet light, and redox chemical reactions. A solution of the above ingredients may be added to an initiator solution at a temperature suitable for generating free radicals, for instance about 50-90° C. An initiator may be prepared by dissolving an initiator in an organic or aqueous solvent. A suitable class of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator.

In one embodiment, the binder polymer is made by combining a first aqueous monomer solution including a reducing polymerization initiator with a second aqueous monomer solution including an oxidizing polymerization initiator, wherein the initiators react to form a binder coating. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the binder coating is formed in about 100 minutes or less, such as about 60 minutes or less, or about 30 minutes or less, or about 15 minutes or less, or about 10 minutes or less.

The pH of the first and/or second aqueous monomer solution is adjusted to about 4.5 to 8, such as about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to 8, such as about 5.5 to about 7.0. If desired, the pH may be increased after polymerization is complete by addition of a suitable basic solution. The extent of neutralization can be used to adjust the properties of the coating. Greater neutralization of the acid functional components generally provides for greater absorbent capacity, while adhesiveness is generally enhanced with more acid functionality.

The amounts of the polymerization ingredients added to the first and second aqueous solutions are selected so as to produce the binder polymer having the coating described above.

In some aspects, a surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc., a business having offices located in Paterson, N.J. U.S.A.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one particular aspect, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one particular aspect, the oxidizing polymerization initiator includes hydrogen peroxide.

Generally, when the first aqueous monomer solution is combined with the second aqueous monomer solution the reducing polymerization initiator reacts with the oxidizing polymerization initiator (e.g., a redox reaction) thereby initiating a polymerization reaction to form a binder coating including a monoethylenically unsaturated monomer and an ethylenically unsaturated monomer that has post-application, moisture-induced crosslinking capability.

Following polymerization of the binder polymer, a water-soluble plasticizer may be added to the binder polymer solution. Suitable plasticizers include alcohols, polyhydric alcohols such as glycerol and sorbitol, and glycols and ether glycol such as mono- or diethers of polyalkylene glycol, mono- or diester polyalkylene glycols, glycolates, sorbitan esters, esters of citric and tartaric acid, imidazoline derived amphoteric surfactants, lactams, amides, polyamides, quaternary ammonium compounds, glycerol esters, including mono/di/tri-glycerides, and combinations thereof. In some aspects, polyhydric alcohols, polyethylene glycol (with a molecular weight up to about 600), glycerol, sorbitol and mixtures thereof are particularly suitable. In one example, glycerol is particularly desirable. In one example, the plasticizer is nonionic. In another example, the plasticizer is non-volatile. Non-volatile plasticizers are materials that exhibit minimal evaporative loss, such as less than about 10%, under the conditions used to remove highly-volatile components, particularly water. In general, volatile components are materials that exhibit substantial evaporative loss under such conditions.

The blend of binder polymer and plasticizer may be applied to various substrates. Suitable substrates include thermoplastic webs, films, cloths, nonwovens and release paper (for subsequent transfer to articles). The coated substrate is then dried to induce crosslinking to form the adhesive composition, as well as to remove substantially all of the highly-volatile component in the blend. The crosslinking takes place in the presence of the water-soluble plasticizer, which creates a 3-dimensional matrix for the composition. The resultant adhesive composition suitably contains about 10% to about 60% by weight of polymerized binder composition, about 5% to about 85% by weight of a water-soluble plasticizer, such as about 40% to 80% by weight water-soluble plasticizer, and less than 10% by weight highly volatile component, such as about 0% to about 5% by weight highly volatile component. In one example, the highly volatile component is water. In addition to heat, if the chosen plasticizer comprises hydroxyl functionality, the plasticizer may be partially crosslinked into the composition by an alcohol exchange reaction with the alkoxysilane functionality incorporated into the binder polymer.

The adhesive composition of the present invention may be applied to a substrate and subsequently dried to form a cast film. Once the binder polymer is applied to the substrate, crosslinking can be moisture-induced by hydrolysis and condensation of alkoxysilanes. For example, crosslinking of the binder polymer can be induced by concentrating the adhesive composition on the substrate through the removal of the water to promote condensation of silanols generated by hydrolysis of alkoxysilanes. Furthermore, if the substrate material has hydroxyl group functionality on the surface, then the silanols within the binder polymer may react with the hydroxyl to form a covalent bond between the binder polymer and the hydroxyl-containing surface. Non-limiting examples of substrates with hydroxyl surface functionality include glass, sand, or cellulose. In addition, if the non-volatile plasticizer has hydroxyl functionality then the silanols within the binder polymer may react with the hydroxyl to form a covalent bond between the binder polymer and the non-volatile plasticizer. Non-limiting examples of hydroxyl functionality non-volatile plasticizers include glycerol and sorbitol.

The adhesive composition may be applied to the substrate using any suitable application process, including knife-over-roll coating, or roll coating, either in a continuous coverage or a patterned coverage. Printing applications or other suitable application techniques, including gravure printing, screen, and jet printing can also be utilized. The adhesive composition may also be applied to the substrate using a spray application.

In order to provide an adhesive composition having suitable initial and prolonged attachment and easy/painless removal, it may be desirable to measure the ability of the adhesive to quickly attach and securely adhere to a particular surface, such as skin. Such measurements may include parameters such as storage modulus, loss modulus, and Tan (delta) value. In general, the storage modulus (G') describes the elastic character of the adhesive composition. G' is related to adhesive performance properties, such as shear resistance, bonding and debonding behaviors. The elastic properties involve the spring-like response to force. The loss modulus (G") describes the viscous response of the adhesive composition. G" relates to adhesive processing characteristics, such as viscosity and sprayability. The viscous properties involve the liquid-like response to force. Tan(delta) is the ratio of G" to G', at a specified test condition. The Tan(delta) describes the balance required for good adhesion. The liquid-like properties provide conformability to allow good contact while the spring-like properties provide the resistance to force that give adequate peel adhesion. The proper balance also provides for the ability of the adhesive composition to prevent residue of the adhesive on the surface upon removal.

In some aspects, the adhesive composition can have a storage modulus (G') measured at a temperature of 25-degrees Celsius and 1 rad/sec of greater than about 1,000 Pa, such as about 2,500 Pa. In other aspects, the adhesive composition can have a loss modulus measured at a temperature of 25-degrees Celsius and 1 rad/sec of greater than about 1,000 Pa, such as about 1,700 Pa. In still other aspects, the adhesive composition can have a Tan(delta) measured at 25-degrees Celsius of greater than 0.65 rad/sec. In one particular aspect, the adhesive composition contains all three of these parameters (i.e., a G' of greater than about 1,000 Pa, a G" of greater than about 1,000 Pa, and a Tan(delta) greater than 0.65 rad/sec as measured at 25 degrees Celsius.)

It may be desirable to further incorporate certain additives into the adhesive composition which can be utilized to provide benefits to attachment surfaces. By way of example only, these additives can include medications and skin enhancers such as moisturizers (including smoothing and wrinkle removing), antioxidants (including anti-aging), lipids (including barrier replenishment), and botanicals. In some aspects, such additives can function as the plasticizer component for the adhesive composition. In other aspects, such additives can be blended with the plasticizer component, such as those described above. For example, it may be particularly suitable to blend at least one skin enhancing additive with glycerol.

Suitable moisturizing additives include glycerin, propylene glycol, lactic acid and its salts, glycolic acid and its salts, hydrolyzed proteins, hyaluronic acid, sodium hyaluronate, salicylic acid, phospholipids, glycerol and glycerol containing compounds, glyceryl polymethacrylate, propylene glycol, collagen, urea/urea compounds, pyrrolidone carboxylic acid (PCA) and its salts, sorbitol, hydrolyzed starch hydrolysates, honey, mannitol and other sugars (including oligosaccharide aldonic acid, lactobionic acid (including 4-O—B-D-galactopyranosyl-D-gluconic acid), trehalose, and xylitol), diglycerol, glycerol tridecanoate, glycerol trimyristate, glycerol tristearate, and polyglycerol-3 fatty acid esters.

Suitable antioxidant additives include flavonoids, lycopene (beta-carotene), lipoic acid, alpha-linoleic acid, vitamin C, alpha-tocopherol, ascorbate (including sodium ascorbate, calcium ascorbate, potassium ascorbate, and ascorbyl palmitate), tocopherols (including dl-alpha-tocopherol, gamma-tocopherol, and delta-tocopherol), gallates (including propyl gallate, octyl gallate, and dodecyl gallate), erthorbic acid, sodium erythorbate, tert-butylhydroquinone, butylated hydroxyanisole, and butylated hydroxytoluene.

Suitable lipid additives include cholesteryl sulfate, neutral lipids, free sterols, free fatty acids, triglycerides, sterol/wax esters, squalane, sphingolipids, glucosylceramides, ceramides, hydrogenated lecithin and cholesterol, and vegetable-derived oils.

Suitable botanicals include xylitol, vitamin E, acacia extract, althea root extract, arnica extract, borage extract, calendula extract (marigold), chamomile extract, clove extract, clover blossom extract, comfrey extract, cranberry extract, dandelion extract, dulse extract, elderberry extract, fennel extract, ginseng root extract, hibiscus extract, irish moss extract, ivy extract, jasmine extract, kelp extract, lavender extract, linden flower extract, meadow sweet extract (mayflower), melilot extract (hayflower), oatmeal extract, oatmeal extract, orange flower extract, orange peel extract, parsley extract, passion fruit extract, peach extract, peppermint extract, peppermint extract, primrose extract, quince seed extract, rose hips extract, sage extract, sambucus elder extract, sambucus elder extract, slippery elm bark extract, southernwood extract, spearmint extract, violet extract, walnut extract (black), white willow bark extract, yarrow extract, and yucca extract.

Medicated patches that utilize the adhesive composition of the present invention as a delivery vehicle are also potential products. Potential medications include, but are not limited to, anti-virals such as immunomodulators, including imiquimod, imiquimod derivatives, podofilox, podophyllin, interferon alpha, reticolos, cidofovir, and nonoxynol-9; and anti-inflammatory agents, such as aspirin, ibuprofen, indomethacin, phenylbutazone, bromfenac, fenamate, sulindac, nabumetone, and ketorolac.

Other potential products include personal care articles including disposable absorbent articles such as diapers, sanitary napkins, pantiliners, tampons, perspiration pads. Absorbent articles often contain an absorbent core. The adhesive composition of the present invention can be used beneficially on such disposable absorbent articles which are applied directly to the skin of a user. The adhesive composition is also suitable for use on human waste management devices such as urine, menstrual and fecal management devices with bags having an aperture and a flange surrounding the aperture for adhesive attachment to the uro-genital area and or the perianal area of a wearer.

The adhesive may also find application to attach articles to the skin such as protective articles such as genital-, knee- or elbow-protectors or bandages; clothing such as bras, surgical gowns, or parts of garments during fitting at a tailor; nasal plasters; prosthesis such as breast replacements or wigs; cold-wraps (e.g., to provide pain relief from bruises and to reduce swelling); thermal wraps (e.g., to provide relief of temporary and chronic pain); protective face masks (e.g., for the reduction or prevention of inhalation of noxious substances); anti-snoring patches, ornamental articles such as jewelry, earrings, guises, tattoos; goggles or other eye wear, tapes, bandages, dressings of general utility, wound healing and wound management devices; and biomedical skin electrodes such as ECG, EMG, EEG, TENS electrosurgery, defibrillation, EMS and electrodes for facial/beauty applications; and fixation products and/or devices intended to affix patient catheters, tubing, leadwires, cables, and the like.

The present invention may be better understood with reference to the following examples.

EXAMPLES

Example 1

A binder polymer was prepared by mixing two monomer solutions. A first monomer solution (Solution No. 1) was prepared by combining 79 grams (1.096 moles) of acrylic acid with 10.5 grams polyethylene glycol (mol. wt.=200) while stirring with a magnetic stir bar at room temperature. This solution was then added to a solution of 17.5 grams of sodium hydroxide (0.437 moles) dissolved in 160 grams of water while cooling in an ice bath. Then, 0.50 grams ($2.83 \times 10^{-3}$ moles) of ascorbic acid was added to the solution while continuing to stir.

A second monomer solution (Solution No. 2) was prepared by adding 10.5 grams polyethylene glycol (mol. wt.=200) to 50 grams of water while stirring with a magnetic stir bar at room temperature. Then, 1.6 ml ($8.67 \times 10^{-3}$ moles) of 3-(trimethoxysilyl)propyl methacrylate and 0.57 ml of 30% aqueous hydrogen peroxide were added while continuing to stir to produce a clear solution.

A neutralization solution was then prepared by dissolving 12 grams (0.3 moles) sodium hydroxide in 160 grams of water.

A polymerization reaction was initiated to form the binder polymer by adding Solution No. 2 to Solution No. 1 while stirring with a magnetic stir bar while cooling in an ice bath. The polymerization reaction began within one minute of mixing, as was indicated by a visual increase in viscosity. 200 grams of water was then added slowly over five minutes to keep the viscosity in a range that provided for continued mixing with a spatula. A maximum polymerization temperature of 62° C. was observed about 8 minutes after mixing of the two monomer solutions. After about 20 minutes the sodium hydroxide neutralization solution was added while stirring in an ice bath to neutralize the binder polymer to about 70%.

The resulting aqueous binder polymer was cast into a film by pouring 14.23 grams of the polymer into a polystyrene weigh boat and allowing the water to evaporate overnight in a hood at room temperature, followed by drying at 80° C. for 30 minutes. The resulting film weighed 2.79 grams, indicating a solution concentration of about 19.6%.

An adhesive composition suitable for skin adhesion was then prepared by blending 58 grams of the binder polymer solution with 34 grams of glycerol. The blend was poured into 3 polypropylene weighing dishes and placed in a Model No. DK-63 laboratory oven (available from Scientific Products, a division of Baxter Diagnostics, a business having offices located in McGaw Park, Ill. U.S.A.) at 60° C. for about 16 hours followed by further heating at 80° C. for 45 minutes. The resultant crosslinked adhesive film had a composition of about 25% absorbent binder polymer and 75% glycerol plasticizer. The average thickness was about 1.15 mm. The adhesive was evaluated qualitatively and found to have high adhesion to skin and very high cohesive strength, as a result of the crosslinked structure formed upon water removal. It was also noted that the samples could be removed without pain from hairy forearms.

A sample of the adhesive composition was also prepared as described above, but was dried onto silicone release paper rather than in a polypropylene weighing dish. The resulting crosslinked adhesive film was then used for determination of the viscoelastic properties. To measure such properties, an Advanced Rheometric Expansion System (ARES) Rheometrics Scientific rheometer (available from TA Instruments, a business having offices located in New Castle, Del. U.S.A.) was utilized. The following values were obtained at 25° C.

and 1 rad/second: storage modulus (G')=2500 Pa, loss modulus (G")=1770 Pa. The Tan(delta) from 1 to 100 rad/second ranged from 0.2 to 0.7.

Example 2

A second binder polymer was prepared using the method described in EXAMPLE 1 above. The resultant composition had a polymer concentration of 20%. 60 grams of the binder polymer was combined with 22.5 grams of glycerol. The blend was spread onto a polyester film (0.55 mm thick), and dried in the DK-63 oven for about 16 hours at 80° C. to provide an adhesive composition comprising about 65% binder polymer and 35% glycerol. The sample was equilibrated for 24 hours at 50% relative humidity and then used to determine peel adhesion from dry skin.

The peel adhesion from the forearms from four volunteers was tested. The polyester film coated with adhesive composition was cut to a width of 3.81 cm and was placed on the inside forearm of each volunteer such that the adhesive was in contact with the skin. The coated film was then pressed down onto the skin using a 1 kg roller and rolling once in each direction. The adhesive was peeled from the forearm at a 90 degree angle using a tensile tester at a speed of 300 mm/minute (using the Peel Test described below). The average peel force was about 1.5N, or 0.4 N/cm.

Example 3

A third binder polymer was prepared as describe in EXAMPLE 1 with a polymer concentration of 24.8%. A first adhesive composition (Adhesive A) was prepared by combining 32.5 grams of the binder polymer with 18.5 grams of glycerol and 3 grams of RHOPLEX B-15R hydrophobic polymer dispersion at a concentration of 46% by weight, available from Rohm and Haas, a business having offices located in Philadelphia, Pa. U.S.A.

A second adhesive composition (Adhesive B) was prepared by combining 32.5 grams of the binder polymer with 18.5 grams of glycerol and 10 grams of RHOPLEX B-15R.

These blends were spread onto a polyester film (0.55 mm thick), and dried in the DK-63 oven for 2 hours at 100° C. The resultant adhesives have the compositions shown TABLE 1 below.

TABLE 1

| Sample | Absorbent Binder Polymer | Glycerol | Hydrophobic Polymer |
| --- | --- | --- | --- |
| Adhesive A | 28.8% | 66.2% | 5.0% |
| Adhesive B | 25.9% | 59.4% | 14.8% |

The addition of a discontinuous phase of hydrophobic polymer was found to be beneficial for adhesion to oily skin. This concept has been further described in EP 1163309 B1 to Munro et al., which is incorporated herein by reference in a manner that is consistent herewith.

Example 4

A fourth binder polymer was prepared as describe in EXAMPLE 1, except the post-polymerization neutralization was not performed so that the polymer had 30 mole percent of the acrylic acid neutralized to the sodium salt and 70% remained in the acid form. The solution had a polymer concentration of 17%.

An adhesive composition was then prepared by combining 29.4 grams of the binder polymer solution with 11.2 grams of glycerol. The blend was then dried in the DK-63 oven at 80° C. for 24 hours. The resultant adhesive composition provided a skin adhesive qualitatively assessed to be higher in adhesion than the more neutralized versions above.

Example 5

Skin adhesives that may inhibit the growth of micro organisms were prepared by utilizing a binder polymer that comprised quaternary ammonium groups. To prepare such a polymer, two monomer solutions were prepared separately. The first monomer solution (S-1) was prepared by dissolving 41.5 grams of a 2-acrylamido-2-methyl-1-propane sulfonic acid (0.20 moles) in 80 25 grams of deionized water and then neutralizing it with a solution of 8 grams of sodium hydroxide in 100 grams of deionized water. Then 0.18 grams (1.02× $10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

The second monomer solution (S-2) was prepared by adding 30 grams of deionized water, 0.37 ml of 30% aqueous hydrogen peroxide and 1.0 ml (5.42×$10^{-3}$ moles) of 3-(trimethoxysilyl)propyl methacrylate to 55.0 grams of a 75% solution of (3-acrylamidopropyl) trimethyl ammonium chloride (0.20 moles).

A polymerization reaction was initiated to form the binder polymer by adding S-2 to S-1 while stirring with a magnetic stir bar while cooling in an ice bath. The result was an 8.7% solution of quaternary absorbent binder polymer.

57.5 grams of the 8.7% solution of quaternary absorbent binder polymer was blended with 15 grams of glycerol. The composition was then spread onto release paper, and was dried in the DK-63 oven at 80° C. for 24 hours. The resultant adhesive film had a composition of about 25% by weight quaternary absorbent binder polymer and 75% by weight glycerol plasticizer. It was qualitatively observed that the adhesive composition provided good adhesion to skin with clean removal.

TEST METHODS

Rheology

The rheology of hydrogels was measured at 25° Celsius using an ARES Rheometric Scientific oscillatory rheometer or the equivalent. A sample having a thickness of approximately 1 mm and diameter of 25 mm was aged for at least 24 hours. The sample was then placed between the two insulated Parallel Plates of 25 mm diameter, controlled at a temperature of approximately 25° C. A Dynamic Frequency Sweep was performed on the hydrogel in strain mode at an applied strain within the linear elastic response of the hydrogel (e.g., up to a strain of about 10%), with measurements at discrete frequency values between 0.1 and 100 rad/sec. Results were obtained as G', G" and Tan(delta) at frequency values of 1.0 and 100 rad/sec.

Peel Force on Dry Skin Test

The peel force to remove the adhesive compositon from dry skin was measured using a suitable tensile tester, for example an ALLIANCE RT/1 frame run with TESTWORKS 4 software (available from MTS Systems Corporation, with offices in Cary, N.C., USA.) equipped with a 100N load cell. Samples were cut into strips of width 38.1 mm and length between about 10 and 20 cm. A non-stretchable film having a length longer than the adhesive sample was applied to the reverse side of the adhesive sample (e.g., the substrate side) using double sided tape.

For samples tested with release paper, the release paper was removed prior to applying the adhesive sample to the forearm and then rolling it into place using a compression weight roller to prevent air entrapment between the adhesive composition and skin. The roller had a diameter of 13 cm, a width of 4.5 cm and a mass of 1 Kg. It was covered in rubber of 0.5 mm thickness.

The free end of the backing film was attached to the upper clamp of the tensile tester and the person's arm was placed below. The sample was peeled from the skin at an angle of 90 degrees and at a rate of 300 mm/min. The average peel value obtained during the peeling of the whole sample was obtained as the peel value in·N/cm. The average of triplicate measurements was reported.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An adhesive composition comprising a water-soluble binder polymer and a water-soluble plasticizer; wherein said binder polymer includes about 15-99.8% by weight of monoethylenically unsaturated polymer units; about 0.1-20% by weight polyacrylate ester units that include an alkoxysilane functionality; and about 0.1-75% by weight polymer units selected from polyolefin glycol units, polyolefin oxide units, or combinations thereof.

2. The adhesive composition of claim 1 wherein said water-soluble plasticizer is non-volatile.

3. The adhesive composition of claim 1 wherein said water-soluble plasticizer is selected from the group consisting of alcohols, glycols, glycolates, sorbitan esters, esters of citric and tartaric acid, imidazoline derived amphoteric surfactants, lactams, amides, polyamides, quaternary ammonium compounds, glycerol esters, and combinations thereof.

4. The adhesive composition of claim 1 wherein said water-soluble plasticizer is selected from the group consisting of polyhydric alcohols, polyethylene glycol, glycerol, sorbitol and combinations thereof.

5. The adhesive composition of claim 1 wherein said water-soluble plasticizer is present in an amount between about 5% and about 85% by weight.

6. The adhesive composition of claim 5 wherein said water-soluble plasticizer is present in an amount between about 40% to about 80% by weight.

7. The adhesive composition of claim 1 further comprising less than 10% by weight of a highly volatile component.

8. The adhesive composition of claim 7 wherein said highly volatile component is water.

9. The adhesive composition of claim 1 further comprising a highly volatile component in an amount between about 0% and about 5% by weight.

10. The adhesive composition of claim 9 wherein said highly volatile component is water.

11. The adhesive composition of claim 1 wherein said adhesive composition is crosslinked.

12. The adhesive composition of claim 1 wherein said water-soluble plasticizer comprises glycerol and at least one additive selected from the group consisting of moisturizers, antioxidants, lipids, botanicals, medications, and combinations thereof.

13. The adhesive composition of claim 1 further comprising about 5% to about 15% by weight hydrophobic polymer.

14. The adhesive composition of claim 1 having a Peel value from dry skin of at least 0.2N/cm.

15. An article comprising the adhesive composition of claim 1.

16. The article of claim 15 wherein said article is selected from the group consisting of personal care articles, heath/medical articles, and household/industrial articles.

17. The adhesive composition of claim 1 having a storage modulus (G') at 25 degrees Celsius and 1 rad/sec of at least about 1000 Pa.

18. The adhesive composition of claim 17 having a storage modulus (G") at 25 degrees Celsius and 1 rad/sec of at least about 2500 Pa.

19. The adhesive composition of claim 1 having a loss modulus (G") at 25 degrees Celsius and 1 rad/sec of at least about 1000 Pa.

20. The adhesive composition of claim 19 having a loss modulus (G") at 25 degrees Celsius and 1 rad/sec of at least about 1770 Pa.

21. The adhesive composition of claim 1 having a Tan (delta) at 25 degrees of at least about 0.65.

22. The adhesive composition of claim 21 further comprising a highly volatile component in an amount between about 0% and 5% by weight.

23. The adhesive composition of claim 21 wherein said highly volatile component is water.

24. The adhesive composition of claim 21 wherein said water-soluble plasticizer comprises glycerol and at least one additive selected from the group consisting of moisturizers, antioxidants, lipids, botanicals, and combinations thereof.

25. An adhesive composition comprising a water-soluble binder polymer and a water-soluble plasticizer;
    wherein said binder polymer is made by combining a first aqueous monomer solution including a reducing polymerization initiator with a second aqueous monomer solution including an oxidizing polymerization initiator;
    wherein said first aqueous monomer solution further includes a monoethylenically unsaturated monomer and an ethylenically unsaturated monomer that contains an alkoxysilane functionality;
    wherein said second aqueous monomer solution includes a monoethylenically unsaturated monomer; and
    wherein said reducing polymerization initiator and said oxidizing polymerization initiator react to form said binder polymer.

26. The adhesive composition of claim 25 wherein at least one of said monomer solutions comprises a template polymer selected from the group consisting of polyolefin glycol and polyolefin oxide.

27. An adhesive composition of claim 25 wherein said binder polymer is formed in about 100 minutes or less.

* * * * *